United States Patent
Hasegawa et al.

(10) Patent No.: US 7,235,701 B2
(45) Date of Patent: Jun. 26, 2007

(54) PROCESS FOR PRODUCING ALDEHYDE

(75) Inventors: Shoji Hasegawa, Wakayama (JP); Toru Nishimura, Wakayama (JP); Osamu Tabata, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/144,942

(22) Filed: Jun. 6, 2005

(65) Prior Publication Data

US 2005/0272958 A1 Dec. 8, 2005

(30) Foreign Application Priority Data

Jun. 7, 2004 (JP) ............................. 2004-168010

(51) Int. Cl.
- C07C 45/29 (2006.01)
- B01J 23/00 (2006.01)
- C23C 16/00 (2006.01)

(52) U.S. Cl. ...................... 568/471; 502/313; 502/314; 502/326; 427/248.1

(58) Field of Classification Search ................ 568/471
See application file for complete search history.

(56) References Cited

U.S. PATENT DOCUMENTS

| 3,256,339 A | 6/1966 | Cole et al. ................. 260/603 |
| 4,132,668 A * | 1/1979 | Gryaznov et al. ............. 502/4 |
| 4,154,762 A | 5/1979 | Huang et al. ............... 260/586 |
| 4,743,577 A | 5/1988 | Schroeder et al. .......... 502/326 |
| 5,055,537 A * | 10/1991 | Kawata et al. ............. 526/240 |
| 2003/0159799 A1 | 8/2003 | Bröcker et al. ................ 165/4 |

FOREIGN PATENT DOCUMENTS

| EP | 0 218 124 A1 | 4/1987 |
| EP | 0 529 804 A2 | 3/1993 |
| GB | 1 381 587 | 1/1975 |
| JP | 62-21574 | 5/1987 |
| JP | 7-34865 | 4/1995 |

* cited by examiner

Primary Examiner—Sikarl A. Witherspoon
(74) Attorney, Agent, or Firm—Oblon, Spivak, McClelland, Maier & Neustadt, P.C.

(57) ABSTRACT

The invention provides a film-type dehydrogenation reaction catalyst for aldehyde production, which is used in producing an aldehyde from an alcohol as a starting material, as well as a process for producing an aldehyde, which includes reacting an alcohol in the presence of the film-type dehydrogenation reaction catalyst.

11 Claims, No Drawings

PROCESS FOR PRODUCING ALDEHYDE

FIELD OF THE INVENTION

The present invention relates to a film-type dehydrogenation reaction catalyst for aldehyde production and to a process for producing an aldehyde by using the same.

BACKGROUND OF THE INVENTION

Fatty aldehydes produced from tallow, coconut oil, palm oil etc. as the starting material are important intermediates in household and industrial fields, and are utilized in a wide variety of applications such as the field of perfume.

Conventionally, there is a method of producing an aldehyde from an alcohol as the starting material by dehydrogenation reaction or oxidation reaction. For example, JP-B 7-34865 discloses a method of preparing a target carbonyl compound (aldehyde or ketone) through dehydrogenation reaction by using a Cu/Fe/Al/(alkali metal and/or alkaline earth metal)/Zn catalyst. When such a catalyst is used, the product can be obtained with a high selectivity. But any technique such as stirring for effectively mixing the starting materials with the catalyst is required because of a suspended bed system using such a powdery catalyst. The product should be separated, for example, by filtration from the catalyst. Such problems make facilities and operations complicated.

On the other hand, a fixed bed system can be mentioned as a process neither requiring the operation of mixing the catalyst by stirring or gas bubbling nor necessitating separation by filtration.

As one form of the catalyst used in a fixed bed system, a pellet-, noodle- or tablet-shaped molded catalyst has been well known. A catalytically active substance in a powdery form can be molded into the above form by a method such as compression or extrusion, to form a structure having numberless pores thereby attaining a bulk form and high surface area simultaneously.

As another form of the catalyst used in a fixed bed system, a honeycomb-shaped catalyst is known. JP-B 62-21574 discloses a catalyst in the form of a structure having a large number of flow paths in the direction of from the inlet to outlet of a fluid, which are separated from one another by a thin wall, for example a pipe, a honeycomb, a plate or the like.

SUMMARY OF THE INVENTION

The present invention relates to a film-type hydrogenation reaction catalyst for aldehyde production, which is used in producing an aldehyde from an alcohol as the starting material, as well as a process for producing an aldehyde, which includes reacting an alcohol in the presence of the film-type hydrogenation reaction catalyst.

The present invention relates to use of the above shown film-type catalyst for dehydrogenation reaction to produce an aldehyde from an alcohol.

DETAILED DESCRIPTION OF THE INVENTION

When a product is to be obtained by using a molded catalyst of a conventional fixed bed catalyst in this reaction, undesired byproducts are formed. The undesired byproducts include wax and aldol condensates generated by side reaction of an alcohol as the starting material. Various technical modifications for carrying out the reaction highly selectively by suppressing these byproducts have been conducted, but it has been difficult to carry out this reaction highly selectively in a simple process. That is, high productivity and high selectivity could not be simultaneously satisfied.

In the Examples in JP-B 62-21574, olefins are dehydrogenated by gaseous phase reaction at 600 to 640° C., but it is not described therein that an alcohol is dehydrogenated by gaseous phase reaction at about 200° C. to obtain an aldehyde. Although it is described therein that suppression of side reactions is advantageous, it is only suggested that the suppression can be attributed to a reduction in the total pressure in the reaction system by the use of a catalyst of such a structure securing a flow path for the reaction substance and reducing a pressure drop.

The present invention provides a production method wherein an alcohol is used as a starting material to produce the corresponding aldehyde with high yield by a simple process, as well as a catalyst used therein.

According to the present invention, the objective aldehyde can be obtained highly selectively by a simple process neither requiring a special mixing operation nor necessitating the operation of separating the catalyst.

The starting material alcohol used in the process for producing an aldehyde according to the present invention includes linear or branched C6 to C36 saturated or unsaturated fatty alcohols. Specific examples include hexyl alcohol, octyl alcohol, lauryl alcohol, myristyl alcohol, stearyl alcohol, behenyl alcohol, oleyl alcohol etc. and mixed alcohols thereof, a Ziegler alcohol obtained by the Ziegler process, oxo alcohol obtained by an oxo method, Guerbet alcohol, etc. These alcohols may be used alone or as a mixture of two or more thereof.

The film-type dehydrogenation reaction catalyst used in the present invention is different from a conventional catalyst of an unordered packing type having a size of several millimeters, and refers to a catalyst of 1 mm or less in thickness in the form of film. The process of transferring the reaction starting material and the product in the inside of the catalyst is governed by diffusion, and by reducing the transfer distance to 1 mm or less, the transfer of the substance between the inside and outside of the catalyst can be promoted thereby suppressing the over-reaction of the product in the inside of the catalyst. That is, the thickness of the catalyst layer of the film-type catalyst is very important in the present invention, and the thickness of the catalyst layer is preferably 400 μm or less, more preferably 100 μm or less, still more preferably 50 μm or less, further more preferably 30 μm or less. The lower limit of the thickness is preferably 0.01 μm or more, still more preferably 1 μm or more in order to secure the strength of the catalyst layer and attain the durability of the strength.

The structure of the film-type catalyst is in various shapes, depending on the shape of a reactor. Examples include a catalyst coating layer formed on a tubular wall surface, a catalyst molded into thin layers dividing the space of a tube into a plurality of flow paths in the axial direction, and can be used preferably in a tube-type flow reactor. The catalyst may be a catalyst coating layer or the like formed on an open fin-shaped flat plate arranged in a tank, and can be used preferably in a tank-type reactor. In either case, the catalyst preferably has a structure to facilitate the supply of the starting reaction material to the catalyst and the recovery of the product from the catalyst. To allow the reaction to advance efficiently, the surface of the catalyst on which the supply of the starting reaction material and the recovery of the product occur is desirably as broad as possible. To achieve this requirement, an assembly including tubes of several millimeters to several ten millimeters in inner diameter bundled therein, or a honeycomb structure with a cell density of several tens to several hundred cells/square inch, provided on its cell internal wall with the film-type catalyst, is preferably used.

To form the film-type catalyst into various structures, there is for example a method of molding the catalyst active substance itself into a honeycomb-shaped structure, but from the viewpoint of attaining both a thin catalyst layer and high mechanical strength, the film-type catalyst is preferably immobilized on the surface of a support. For example, a coating layer containing the catalyst active substance is formed on the surface of a support in the form of a metallic tube or another rigid tube or in the form of a flat plate or a honeycomb as described above to form the film-type catalyst. The coating method used herein may be a conventionally known method, and examples of the coating method include a physical deposition method such as sputtering, a chemical deposition method, a method of impregnation from a solution, and various methods with a binder, such as blade coating, spray coating, dipping coating, spinning coating, gravure coating and die coating.

The active substance constituting the film-type dehydrogenation reaction catalyst is not particularly limited, and known active substances having a catalytic dehydrogenation activity can be used, but generally Cu-based metals or the group 8 metals in the periodic table, such as Ni, Pd and Pt can be preferably used, and particularly Cu-containing metals are more preferable. For example, an active substance containing Cu alone or two-component metal containing Cu and a transition metal element such as Cr, Co, Ni, Fe or Mn can be mentioned, and an active substance containing Cu and Ni is preferably used. An active substance containing 3 or more component metals is also preferably used. An active substance having such metals supported on silica, alumina, titania or zeolite, etc is also be used.

The internal structure of the film-type catalyst depends greatly on the type of the active substance constituting the catalyst, the method of producing the catalyst, etc., and may form a dense continuous phase or may be porous. For example, the catalyst can have a fine dense continuous phase when it is a thin film formed on the surface of a support by sputtering or chemical deposition, or the catalyst can be made porous when it is formed on the surface of a support by wet or dry coating of a powdery active substance.

The film-formed catalyst may contain therein a binder for fixing the active substance therein to form the film-formed catalyst body. The binder itself does not act as an active substance. The binder includes polymers or inorganic compounds having properties including not only an ability to bind active substances together or to bind active substances to the surface of a support but also chemical resistance and heat resistance to endure the reaction environment without adversely affecting the reaction. Examples include cellulose-based resin such as carboxymethyl cellulose and hydroxyethyl cellulose, fluorine-based resin such as poly(tetrafluoroethylene) and poly(vinylidenefluoride), polymer compounds such as urethane resin, epoxy resin, polyester resin, phenol resin, melamine resin, silicone resin etc., and inorganic compound sols such as silica, alumina etc.

The reactor loaded with the film-type catalyst may be in a wide variety of types including conventionally known types. For example, tube-type flow reactor, a tank-type reaction etc. can be mentioned as described above. In the tube-type flow reactor, the reaction can proceed in a continuous or batch system by single pass or circulatory supply in a flow system of recovering the product continuously while supplying the starting reaction material to the film-type catalyst in the tube. The method of supplying the starting reaction material in this case may be either up-flow or down-flow. In the tank-type reactor, the reaction can proceed in a continuous or batch system, if necessary under stirring, with the film-type catalyst arranged inside.

In the present invention, the reaction of alcohol in the presence of the film-type catalyst includes dehydrogenation reaction, oxidation reaction etc., and the conditions for carrying out these reactions vary depending on the types of the starting alcohol, product and catalyst. The starting alcohol may be present in the gaseous phase or liquid phase, and is preferably present particularly in the liquid phase. When the gaseous phase is present in the reaction, the reaction is carried out preferably in an atmosphere of hydrogen, nitrogen and/or a noble gas in order to maintain the catalyst activity. In the reaction in the two (gaseous and liquid) phases, mass transfer between the two phases is promoted desirably by bubbling with hydrogen, nitrogen and/or a noble gas. The gas used can also be recovered and reutilized. By supplying the reaction starting material in a gas/liquid mixed phase to a reaction site where a thin flow path of several millimeters or less in diameter was formed by the film-type catalyst, the above mass transfer-promoting effect can also be obtained. Desirably, the pressure in the system is not significantly higher than normal pressures. The reaction temperature varies depending on the type of catalyst, but it is preferable that the reaction is carried out at a temperature of 150 to 300° C.

Using an alcohol as the starting material, the corresponding aldehyde can be obtained with high selectivity in a simple process by the method of the present invention.

EXAMPLES

Hereinafter, the present invention is described in more detail by reference to the Examples. The examples are described for merely illustrating the present invention and not intended to limit the present invention.

Production Example 1

Production of a Film-Type Catalyst

A film-type catalyst containing a catalyst active substance in a ternary (copper/nickel/ruthenium) system supported on synthetic zeolite was prepared in the following manner.

(1) A 1-L flask was charged with synthetic zeolite, and then with copper nitrate, nickel nitrate and ruthenium chloride previously dissolved in water in such a molar ratio that Cu/Ni/Ru was 4/1/0.01, and the temperature was increased under stirring. 10 wt % aqueous sodium carbonate solution was gradually dropped at 90° C. into the mixture while the pH was controlled in the range of 9 to 10. After aging for 1 hour, precipitates were filtered, washed with water, then dried at 80° C. for 10 hours, and calcined at 600° C. for 3 hours, to give a powdery catalyst active substance. In the resulting catalyst active substance, the proportion of metal oxides was 50 wt %, and the proportion of synthetic zeolite was 50 wt %.

(2) 50 parts by weight of the above catalyst active substance, 50 parts by weight of hydroxyethyl cellulose (SP-500 manufactured by Daicel Chemical Industries, Ltd.) as a binder, and 1600 parts by weight of water were added and mixed with one another in a ball mill to form a coating.

(3) Stainless steel foil (thickness 20 μm, width 10 cm×37.5 cm) was used as a support, coated with the above coating by a bar coater, then dried at 50° C., and contact-bonded by a roll pressing machine, to fix the film-type catalyst of 12 μm in thickness on both sides of the stainless steel foil. The weight of the film-type catalyst including the binder (excluding the stainless steel foil) was 0.30 g (the weight of the catalyst active substance was 0.15 g).

Production Example 2

Production of a Film-Type Catalyst 90 parts by weight of the powdery catalyst active substance obtained in (1) in Production Example 1, 10 parts by weight of hydroxyethyl cellulose (SP-500 manufactured by Daicel Chemical Industries, Ltd.) as a binder, and 300 parts by weight of water were added and mixed with one another in a ball mill to form a coating in the same manner as in (2) in Production Example 1. This coating was applied onto an internal wall of a stainless steel tube of outer diameter 6.35 mm×inner diameter 4.35 mm×length 300 mm and then dried at 50° C. to give a film-type catalyst. The thickness of the film-type catalyst was 30 μm, and the weight thereof including the binder was 0.12 g.

Production Example 3

Production of a Film-Type Catalyst 90 parts by weight of the powdery catalyst active substance obtained in (1) in Production Example 1 were added to 10 parts by weight of pulp fibers (trade name "Mackenzie", CSF 200 ml, manufactured by Fletcher Challenge Canada), and water was added to the mixture such that the concentration as the solids content of the pulp fibers and the catalyst active substance in total became 3 wt %. Then, 0.5 part by weight of a cationic flocculating agent (polyamide epichlorohydrin resin, trade name "WS4020", manufactured by Seiko PMC Co., Ltd.) and 0.25 part by weight of an anionic flocculating agent (sodium carboxymethyl cellulose, trade name "Cellogen WS-C" manufactured by Dai-ichi Kogyo Seiyaku Co., Ltd.) were added to, and sufficiently mixed with, 100 parts by weight of the above solids content. Then, the resulting mixture was diluted with water to 0.5 wt %, then formed into paper by a rectangular sheet machine of width 250 mm×250 mm (manufactured by Kumagaya Riki Kogyo Co., Ltd.) according to JIS P8209, to prepare a sheet-shaped paper molded product in a wet state. Then, the product was dried under the conditions of 200° C. and 3 MPa so as to reduce the water content to 1 wt % or less, to give a film-type catalyst having the catalyst active substance supported in it. The content of the catalyst active substance in the resulting film was 65 wt %, and the thickness of the film was 360 μm.

Comparative Production Example 1

Production of a Pellet-Shaped Catalyst

A catalyst was prepared according to a method described in Example 1 in JP-B 7-68153. That is, a hydrolyzed product of tetraisopropyl titanate $\{[(CH_3)_2CHO]_4Ti\}$ was used as a starting material of support, and an aqueous mixed solution of copper nitrate and zinc nitrate and 10 wt % aqueous sodium carbonate solution were mixed therewith at 98° C. under stirring to give slurry having a pH value of 9. From this slurry, precipitates were separated by filtration, then sufficiently washed with water and dried.

Then, the resulting powder consisting of a catalyst active substance was tabletted in a cylindrical form of φ3 mm×height 3 mm and then calcined at 450° C. for 2 hours to give a pellet-shaped catalyst. The proportion of metal oxides in the resulting catalyst active substance was 50 wt % (CuO, 47.5 wt %; ZnO, 2.5 wt %), and the proportion of titanium oxide was 50 wt %.

Example 1

The film-type catalyst obtained in Production Example 1 was corrugated, then stacked alternately with uncorrugated planar part, subjected to activation treatment, charged into a stainless steel cage, and arranged in a 2-L glass separable flask used as a batch reactor. 500 g lauryl alcohol (KALCOL 20 manufactured by Kao Corporation) was charged into it, and the atmosphere in the system was replaced by nitrogen supplied through a glass gas-blowing tube. Thereafter, the flow rate of nitrogen was increased to 15 NL/hr, and stirring with a crescent stirring blade was initiated. The temperature was increased to 220° C., and after 220° C. was reached, samples were taken in the course of time. Analysis was conducted by gas chromatography, and as a result of quantification by an area percentage method, no byproduct was detected at the time of formation of 2% aldehyde, and the selectivity was 100%. The selectivity was 93% at the time of formation of 4% aldehyde.

Example 2

The film-type catalyst obtained in Production Example 2 was arranged and subjected to activation treatment, and then lauryl alcohol (KALCOL 20 manufactured by Kao Corporation) was supplied at 211 g/hr from the bottom of a tube (up-flow), and the temperature in the tube was increased to 220° C. After 220° C. was reached, samples were taken in the course of time. Analysis was conducted by gas chromatography, and as a result of quantification by an area percentage method, the selectivity was 98% at the time of formation of 2% aldehyde. The selectivity was 95% at the time of formation of 4% aldehyde.

Example 3

The film-type catalyst obtained in Production Example 3 was subjected to activation treatment, loaded into a stainless steel cage, and arranged in a 2-L glass separable flask used as a batch reactor. The amount of the catalyst active substance was 0.21 wt % based on the starting alcohol. 500 g lauryl alcohol (KALCOL 20 manufactured by Kao Corporation) was charged into it, and the atmosphere in the system was replaced by nitrogen supplied through a glass gas-blowing tube. Thereafter, the flow rate of nitrogen was increased to 15 NL/hr, and stirring with a crescent stirring blade was initiated. The temperature was increased to 220° C., and after 220° C. was reached, samples were taken in the course of time. Analysis was conducted by gas chromatography, and as a result of quantification by an area percentage method, the selectivity was 80% at the time of formation of 2% aldehyde. The selectivity was 66% at the time of formation of 4% aldehyde.

Comparative Example 1

The pellet-type catalyst obtained in Comparative Production Example 1 was subjected to activation treatment, loaded into a stainless steel cage, and arranged in a 2-L glass separable flask used as a batch reactor. The amount of the catalyst active substance was 0.21 wt % based on the starting alcohol. 500 g lauryl alcohol (KALCOL 20 manufactured by Kao Corporation) was charged into it, and the atmosphere in the system was replaced by nitrogen supplied through a glass gas-blowing tube. Thereafter, the flow rate of nitrogen was increased to 15 NL/hr, and stirring with a crescent stirring blade was initiated. The temperature was increased to 220° C., and after 220° C. was reached, samples were taken in the course of time. Analysis was conducted by gas chromatography, and as a result of quantification by an area percentage method, the selectivity was 54% at the time of formation of 2% aldehyde. The selectivity was 50% at the time of formation of 4% aldehyde.

The reaction conditions and the results in Examples 1 to 3 and Comparative Example 1 are collectively shown in Table 1.

TABLE 1

|  | Example 1 | Example 2 | Example 3 | Comparative example 1 |
|---|---|---|---|---|
| Form of catalyst | Film type | Film type | Film type | Pellet type |
| Kind of catalyst | Cu/Ni/Ru | Cu/Ni/Ru | Cu/Ni/Ru | Cu/Zn |
| Amount of catalyst active substance in film | 50 wt % | 90 wt % | 65 wt % | — |
| Thickness of catalyst or size | 12 μm | 30 μm | 360 μm | size φ 3 mm × H 3 mm |
| Reaction type | Batch type | Up flow (1 pass) | Batch type | Batch type |
| Amount of catalyst active substance | 0.03 wt % (based on starting material) | Coating amount 0.11 g | 0.21 wt % (based on starting material) | 0.21 wt % (based on starting material) |
| Starting alcohol | Lauryl alcohol | Lauryl alcohol | Lauryl alcohol | Lauryl alcohol |
| Amount of starting material charged | 500 g | — | 500 g | 500 g |
| Rate of feeding starting material | — | 211 g/Hr | — | — |
| Flow rate of gas | $N_2$ 15 NL/Hr | No gas | $N_2$ 15 NL/Hr | $N_2$ 15 NL/Hr |
| Reaction temperature | 220° C. | 220° C. | 220° C. | 220° C. |
| Reaction pressure | Atmospheric pressure | Atmospheric pressure | Atmospheric pressure | Atmospheric pressure |
| Selectivity *[1] | 100 | 98 | 80 | 54 |
| Selectivity *[2] | 93 | 95 | 66 | 50 |

*[1] Aldehyde selectivity at the time of formation of 2% aldehyde
Aldehyde selectivity [%] = amount of formed aldehyde/amount of reacted alcohol × 100
*[2] Aldehyde selectivity at the time of formation of 4% aldehyde
Aldehyde selectivity [%] = amount of formed aldehyde/amount of reacted alcohol × 100

The invention claimed is:

1. A dehydrogenation reaction catalyst for aldehyde production, which is used in producing an aldehyde from a linear or branched C6 to C36 saturated or unsaturated fatty alcohol as a starting material,
   wherein the dehydrogenation reaction catalyst is in the form of a film having a layer comprising a homogeneous mixture of at least one metal and a binder, wherein the film has a thickness of 100 μm or less.

2. The dehydrogenation reaction catalyst according to claim 1, wherein the metal is at least one selected from the group consisting of copper and the group 8 metals in the periodic table.

3. A process for producing an aldehyde, which comprises reacting a linear or branched C6 to C36 saturated or unsaturated fatty alcohol in the presence of the dehydrogenation reaction catalyst according to claim 1.

4. The dehydrogenation reaction catalyst according to claim 1, wherein the binder is an organic binder.

5. The dehydrogenation reaction catalyst according to claim 1, wherein the binder is at least one selected from the group consisting of a cellulose resin, a fluorine-containing resin, and a polymeric resin.

6. The dehydrogenation reaction catalyst according to claim 1, wherein the binder is at least one selected from the group consisting of a carboxymethyl cellulose and a hydroxyethyl cellulose.

7. The dehydrogenation reaction catalyst according to claim 1, wherein the binder is at least one selected from the group consisting of a poly(tetrafluoroethylene) and poly(vinylidenefluoride).

8. The dehydrogenation reaction catalyst according to claim 1, wherein the binder is at least one selected from the group consisting of a urethane resin, an epoxy resin, a polyester resin, a phenol resin, a melamine resin, and a silicone resin.

9. The process for producing an aldehydes according to claim 3, wherein the alcohol is selected from the group consisting of hexyl alcohol, octyl alcohol, lauryl alcohol, myristyl alcohol, stearyl alcohol, behenyl alcohol, oleyl alcohol, and mixtures thereof.

10. The dehydrogenation reaction catalyst according to claim 1, wherein the layer comprising the homogeneous mixture of the binder and the metal is immobilized on the surface of a support, and the layer comprises at least three different metals selected from the group consisting of copper and the group 8 metals in the periodic table.

11. The dehydrogenation reaction catalyst according to claim 1, wherein the layer comprising the homogeneous mixture of the binder and the metal is immobilized on the surface of a support and has a thickness of 50 μm or less, and the layer comprises at least three different metals selected from the group consisting of copper and the group 8 metals in the periodic table.

* * * * *